(12) United States Patent
Oshima

(10) Patent No.: US 11,612,520 B2
(45) Date of Patent: Mar. 28, 2023

(54) PAD

(71) Applicant: Daio Paper Corporation, Ehime (JP)

(72) Inventor: Aya Oshima, Tochigi (JP)

(73) Assignee: Daio Paper Corporation, Ehime (JP)

( * ) Notice: Subject to any disclaimer, the term of this patent is extended or adjusted under 35 U.S.C. 154(b) by 1034 days.

(21) Appl. No.: 16/333,629

(22) PCT Filed: Jul. 19, 2017

(86) PCT No.: PCT/JP2017/026041
§ 371 (c)(1),
(2) Date: Mar. 15, 2019

(87) PCT Pub. No.: WO2018/061417
PCT Pub. Date: Apr. 5, 2018

(65) Prior Publication Data
US 2019/0216658 A1     Jul. 18, 2019

(30) Foreign Application Priority Data
Sep. 29, 2016 (JP) .............................. JP2016-192288

(51) Int. Cl.
*A61F 13/15* (2006.01)
*A61F 13/49* (2006.01)
(Continued)

(52) U.S. Cl.
CPC .............. *A61F 13/49* (2013.01); *A61F 13/15* (2013.01); *A61F 13/47* (2013.01); *A61F 13/511* (2013.01);
(Continued)

(58) Field of Classification Search
CPC ........ A61F 13/49; A61F 13/47; A61F 13/511; A61F 13/51104; A61F 13/53;
(Continued)

(56) References Cited

U.S. PATENT DOCUMENTS 6,050,984 A * 4/2000 Fujioka ................. A61F 13/532
604/357
2015/0223997 A1   8/2015 Noda et al.

FOREIGN PATENT DOCUMENTS

CN         1174021        2/1998
CN       101325938       12/2008
(Continued)

OTHER PUBLICATIONS

Extended European Search Report for EP17855375, dated Mar. 16, 2020.
(Continued)

*Primary Examiner* — Jacqueline F Stephens
(74) *Attorney, Agent, or Firm* — Andrus Intellectual Property Law

(57) ABSTRACT

To provide a pad that folds in three in the front-back direction maintaining the shapes of a large number of convex portions protruding on a front-face sheet that prevents the deterioration of liquid diffusibility.

The left front side portion and the left back side portion are folded inward with a first left side folding line which is extending in the front-back direction as the center for the folding and which is provided close to the left side with respect to the left side narrowing edge, and the right front side portion and the right back side portion are folded inward with a first right side holding line which is extending in the front-back direction and which is provided close to the right side with respect to the left side narrowing edge.

6 Claims, 16 Drawing Sheets

(51) Int. Cl.
    *A61F 13/53*     (2006.01)
    *A61F 13/47*     (2006.01)
    *A61F 13/511*     (2006.01)
    *A61F 13/513*     (2006.01)
    *A61F 13/51*     (2006.01)

(52) U.S. Cl.
    CPC ........ *A61F 13/51104* (2013.01); *A61F 13/53* (2013.01); *A61F 2013/1556* (2013.01); *A61F 2013/51078* (2013.01); *A61F 2013/51186* (2013.01); *A61F 2013/51355* (2013.01)

(58) Field of Classification Search
    CPC .... A61F 2013/1556; A61F 2013/51078; A61F 2013/51186; A61F 2013/51355
    See application file for complete search history.

(56) References Cited

FOREIGN PATENT DOCUMENTS

| | | |
|---|---|---|
| CN | 208582603 | 3/2019 |
| EP | 2901978 | 8/2015 |
| JP | H0321238 | 1/1991 |
| JP | 2000-140006 | 5/2000 |
| JP | 2004174234 | 6/2004 |
| JP | 3589528 | 8/2004 |
| JP | 2014076216 | 5/2014 |
| JP | 2015157047 | 9/2015 |

OTHER PUBLICATIONS

International Search Report, PCT/JP2017/026041, dated Oct. 10, 2017.

* cited by examiner

INNER-OUTER
DIRECTION

PAD

CROSS-REFERENCE TO RELATED APPLICATIONS

This application is the U.S. national stage application of International Application PCT/JP2017/026041, filed Jul. 19, 2017, which international application was published on Apr. 5, 2018, as International Publication WO 2018/061417 in the Japanese language. The International Application claims priority of Japanese Patent Application No. 2016-192288, filed Sep. 29, 2016. The international application and Japanese application are both incorporated herein by reference, in entirety.

TECHNICAL FIELD

The present invention relates to a pad to be attached to a tape-type disposable diaper, and more particularly to a pad that is folded in three in the front-back direction in order to maintain convex portions formed to protrude from a front-face sheet.

BACKGROUND ART

It is proposed in the conventional means, in which, convex portions are formed on a front-face sheet to improve the diffusion of urine and the like urinated on an inner surface, the left side portion of an absorber is folded inward with a left imaginary line as the center for the folding to divide the left side portion of the absorber into two in the width direction, the right side portion of the absorber is folded inward with a right imaginary line as the center for the folding to divide the right side portion of the absorber into two in the width direction, the front side portion of the absorber is folded inward with a front side imaginary line as the center for the folding to divide the absorber into three in the front-back direction, and then the back side portion of the absorber is folded inward with a back imaginary line as the center for the folding to divide the absorber into three in the front-back direction. (Patent Literature 1)

Further, in order to prevent the liquid diffusibility from being lowered, the means for forming convex portions arranged by displacing a predetermined pitch in the width direction on the inner surface of the front-face sheet has been proposed. (Patent Literature 2)

CITATION LIST

Patent Literature

Patent Literature 1: JP 2015-157047 A
Patent Literature 2: JP 2004-174234 A

SUMMARY OF INVENTION

Technical Problem

However, according to the means in Patent Literature 1, since the left side portion and the right side portion folded of an absorber overlap with the central portion in the width direction of the absorber, there is a possibility that the shapes of a number of convex portions formed at a part facing the central portion in the width direction of the absorber on a front-face sheet cannot be maintained by pressing on the left side portion and the right side portion of the absorber. Note that Patent Literature 2 does not disclose means for folding a pad.

It is therefore an object of the present invention to provide a pad that folds in three in the front-back direction maintaining the shape of a large number of convex portions protruding on a front-face sheet that prevents liquid diffusibility from being lowered.

Solution to Problem

In order to solve the above problems, there are following aspects.

According to a first aspect, is provided a pad comprising a liquid-pervious front-face sheet, a liquid-impervious back-face sheet, and an absorber disposed between the front-face sheet and the back-face sheet, wherein convex portions are formed to protrude on the front-face sheet, the absorber is formed with a front side portion positioned on a front side in a front-back direction, a narrowing portion positioned in a central portion in the front-back direction, and a back side portion positioned on a back side in the front-back direction, in a planar view, a left front side portion of the front side portion is extended to a left side with respect to a left side narrowing edge of a narrowest portion of the narrowing portion, and a right front side portion of the front side portion is extended to a right side with respect to a right side narrowing edge of the narrowest portion of the narrowing portion, in the planar view, a left back side portion of the back side portion is extended to the left side with respect to the left side narrowing edge of the narrowest portion of the narrowing portion, and a right back side portion of the back side portion is extended to the right side with respect to the right side narrowing edge of the narrowest portion of the narrowing portion, the left front side portion and the left back side portion are folded inward with a first left side folding line, which is extending in the front-back direction as a center for folding and which is provided close to the left side with respect to the left side narrowing edge, the right front side portion and the right back side portion are folded inward with a first right side folding line which is extending in the front-back direction as a center for folding and which is provided close to the right side with respect to the right side narrowing edge, in the planar view, a second folding line extending in a width direction is provided on the front side of two positions at which the absorber is divided into three in the front-back direction, and a third folding line extending in the width direction is provided on the back side of the two positions, the front side portion, in a state where the left front side portion and the right front side portion are folded, is folded inward with the second folding line as a center for folding, or the back side portion, in a state where the left back side portion and the right back side portion are folded, is folded inward with the third folding line as a center for folding, and after that, the back side portion, in a state where the left back side portion and the right back side portion are folded, is folded inward with the third folding line as a center for folding or the front side portion, in a state where the left front side portion and the right front side portion are folded, is folded inward with the second folding line as a center for folding.

According to a second aspect, is provided a pad comprising a liquid-pervious front-face sheet, a liquid-impervious back-face sheet, and an absorber disposed between the front-face sheet and the back-face sheet, wherein convex portions are formed to protrude on the front-face sheet, the absorber is formed with a front side portion positioned on a front side in a front-back direction, a narrowing portion positioned in a central portion in the front-back direction, and a back side portion positioned on a back side in the front-back direction, in a planar view, a left front side portion of the front side portion is extended to a left side with respect to a left side narrowing edge of a narrowest portion of the narrowing portion, and a right front side portion of the front side portion is extended to a right side with respect to a right side narrowing edge of the narrowest portion of the narrowing portion, in the planar view, a left back side portion of the back side portion is extended to the left side with respect to the left side narrowing edge of the narrowest portion of the narrowing portion, and a right back side portion of the back side portion is extended to the right side with respect to the right side narrowing edge of the narrowest portion of the narrowing portion, the left front side portion and the left back side portion are folded inward with a first left side folding line, which is extending in the front-back direction as a center for folding and which is provided close to the left side with respect to the left side narrowing edge, the right front side portion and the right back side portion are folded inward with a first right side folding line which is extending in the front-back direction as a center for folding and which is provided close to the right side with respect to the right side narrowing edge, in the planar view, a second folding line extending in a width direction is provided on the front side of two positions at which the absorber is divided into three in the front-back direction, and a third folding line extending in the width direction is provided on the back side of the two positions, the front side portion, in a state where the left front side portion and the right front side portion are folded, is folded inward with the second folding line as a center for folding, the left front side portion is disposed on an inner side of the first left back side portion extending on the front side with respect to the third folding line in the left back side portion, the right front side portion is disposed on an inner side of the first right back side portion extending on the front side with respect to the third folding line in the right back side portion, and after that, the back side portion, in a state where the left back side portion and the right back side portion are folded, is folded inward with the third folding line as a center for folding.

According to a third aspect, in the configuration of the first or second aspect, the first left side folding line is positioned on the left side narrowing edge, and the first right side folding line is positioned on the right side narrowing edge.

According to a fourth aspect, in the configuration of any one of the first to third aspect, a first left front side overlapping portion and a first right front side overlapping portion each having a rectangular shape are provided at sites overwrapping with the first left side folding line and the first right side folding line, respectively in a front portion of the front side portion, a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

According to a fifth aspect, in the configuration of any one of the first to third aspect, a third left middle side overlapping portion and a third right middle side overlapping portion each having a rectangular shape are provided at sites overlapping with the second folding line on both sides of the narrowing portion, a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

Advantageous Effects of Invention

According to the first aspect, the convex portions are formed to protrude from the front-face sheet. The absorber is formed with the front side portion positioned on the front side in the front-back direction, the narrowing portion positioned in the central portion in the front-back direction, and the back side portion positioned on the back side in the front-back direction. In the planar view, the left front side portion of the front side portion is extended to the left side with respect to the left side narrowing edge of the narrowest portion of the narrowing portion, and the right front side portion of the front side portion is extended to the right side with respect to the right side narrowing edge of the narrowest portion of the narrowing portion. In the planar view, the left back side portion of the back side portion is extended to the left side with respect to the left side narrowing edge of the narrowest portion of the narrowing portion, and the right back side portion of the back side portion is extended to the right side with respect to the right side narrowing edge of the narrowest portion of the narrowing portion. The left front side portion and the left back side portion are folded inward with the first left side folding line which is extending in the front-back direction as the center for the folding and which is provided close to the left side with respect to the left side narrowing edge. The right front side portion and the right back side portion are folded inward with the first right side folding line which is extending in the front-back direction as the center for the folding and which is provided close to the right side with respect to the right side narrowing edge. In the planar view, the second folding line extending in the width direction is provided on the front side of the two positions at which the absorber is divided into three in the front-back direction, and the third folding line extending in the width direction is provided on the back side of the two positions. The front side portion, in the state where the left front side portion and the right front side portion are folded, is folded inward with the second folding line as the center for the folding, or the back side portion, in the state where the left back side portion and the right back side portion are folded, is folded inward with the third folding line as the center for the folding. After that, the back side portion, in the state where the left back side portion and the right back side portion are folded, is folded inward with the third folding line as the center for the folding, or the front side portion, in the state where the left front side portion and the right front side portion are folded, is folded inward with the second folding line as the center for the folding. As a result, the space is formed between the inner surface of the narrowing portion and the inner surface of the back side portion and between the outer surface of the back side portion and the inner surface of the front side portion, and the shapes of the convex portions protruding toward the inside from the front-face sheet facing the front side portion, the narrowing portion, and the back side portion are maintained to prevent the deterioration of liquid diffusibility.

According to the second aspect, in addition to the effect obtained by the first aspect, the convex portions are formed to protrude from the front-face sheet, the absorber is formed with the front side portion positioned on the front side in the front-back direction, the narrowing portion positioned in the central portion in the front-back direction, and the back side portion positioned on the back side in the front-back direction. In the planar view, the front left side portion of the front side portion is extended to the left side with respect to the left side narrowing edge of the narrowest portion of the narrowing portion, and the right front side portion of the front side portion is extended to the right side with respect to the right side narrowing edge of the narrowest portion of the narrowing portion. In the planar view, the left back side portion of the back side portion is extended to the left side with respect to the left side narrowing edge of the narrowest portion of the narrowing portion, and the right back side portion of the back side portion is extended to the right side with respect to the right side narrowing edge of the narrowest portion of the narrowing portion, the left front side portion and the left back side portion are folded inward with the first left side folding line which is extending in the front-back direction as the center for the folding and which is provided close to the left side with respect to the left side narrowing edge, the right front side portion and the right back side portion are folded inward with the first right side folding line which is extending in the front-back direction as the center for the folding and which is provided close to the right side with respect to the right side narrowing edge. In the planar view, at the positions at which the absorber is divided into three in the front-back direction, the second folding line extending in the width direction is provided on the front side of the two positions, and the third folding line extending in the width direction is provided on the back side of the two positions, the front side portion, in the state where the left front side portion and the right front side portion are folded, is folded inward with the second folding line as the center for the folding, the left front side portion is disposed on the inner side of the first left back side portion extending on the front side with respect to the third folding line in the left back side portion, the right front side portion is disposed on the inner side of the first right back side portion extending on the front side with respect to the third folding line in the right back side portion. After that, the back side portion, in the state where the left back side portion and the right back side portion are folded, is folded inward with the third folding line as the center for the folding. As a result, the large space is formed between the inner surface of the narrowing portion and the inner surface of the front side portion. Consequently, the convex portions protruding toward the inside from the front-face sheet facing the front side portion are not pressed by the narrowing portion, and the convex portions protruding toward the inside from the front-face sheet facing the narrowing portion are not pressed by the front side portion. Therefore, it is possible to maintain the shapes of the convex portions protruding toward the inside from the front-face sheet facing the front side portion and the narrowing portion to prevent the deterioration of the liquid diffusibility.

According to the third aspect, in addition to the effect obtained by the first or second aspect, since the first left side folding line is positioned on the left side narrowing edge, and the first right side folding line is positioned on the right side narrowing edge, the left front side portion of the front side portion and the left back side portion of the back side portion are efficiently folded inward along the first left side folding line, and the right front side portion of the front side portion and the right back side portion of the back side portion can be efficiently folded inward along the first right side folding line.

According to the fourth aspect, in addition to the effect obtained by the aspect described in any one of the first to third aspects, at the sites overlapping with the first left side folding line and the first right side folding line in the front portion of the front side portion, the first left front side overlapping portion and the first right front side overlapping portion each having the rectangular shape are provided, and at the sites overlapping with the first left side folding line and the first right side folding line in the front portion of the back side portion, the second left back side overlapping portion and the second right back side overlapping portion each having the top portion in the front side and having the triangle shape are provided, and the second left back side overlapping portion and the second right back side overlapping portion are each extended in the front side with respect to the third folding line so that the large space is formed between the inner surface of the narrowing portion and the inner surface of the front side portion. Consequently, the convex portions protruding toward the inside from the front-face sheet facing the front side portion are not pressed by the narrowing portion, and the convex portions protruding toward the inside from the front-face sheet facing the narrowing portion are not pressed by the front side portion. Therefore, it is possible to further maintain the shapes of the convex portions protruding toward the inside from the front-face sheet facing the front side portion and the narrowing portion and further prevent the deterioration of the liquid diffusibility.

According to the fifth aspect, in addition to the effect obtained by the aspect described in any one of the first to third aspects, at the sites overlapping with the second folding line in both the side portions of the narrowing portion, the third left middle side overlapping portion and the third right middle side overlapping portion each having the rectangular shape are provided, and at the sites overlapping with the first left side folding line and the first right side folding line in the front portion of the back side portion, the second left back side overlapping portion and the second right back side overlapping portion each having the top portion in the front side and having the triangle shape are provided, and the second left back side overlapping portion and the second right back overlapping portion are each extended to the front side with respect to the third folding line so that the large space is formed between the inner surface of the narrowing portion and the inner surface of the front side portion. Consequently, the convex portions protruding toward the inside of the front-face sheet facing the front side portion are not pressed by the narrowing portion, and the convex portions protruding toward the inside of the front-face sheet facing the narrowing portion are not pressed by the front side portion. Therefore, it is possible to further maintain the shapes of the convex portions protruding toward the inside of the front-face sheet facing the front side portion and the narrowing portion and further prevent the deterioration of the liquid diffusibility.

DESCRIPTION OF EMBODIMENTS

Figure 1:
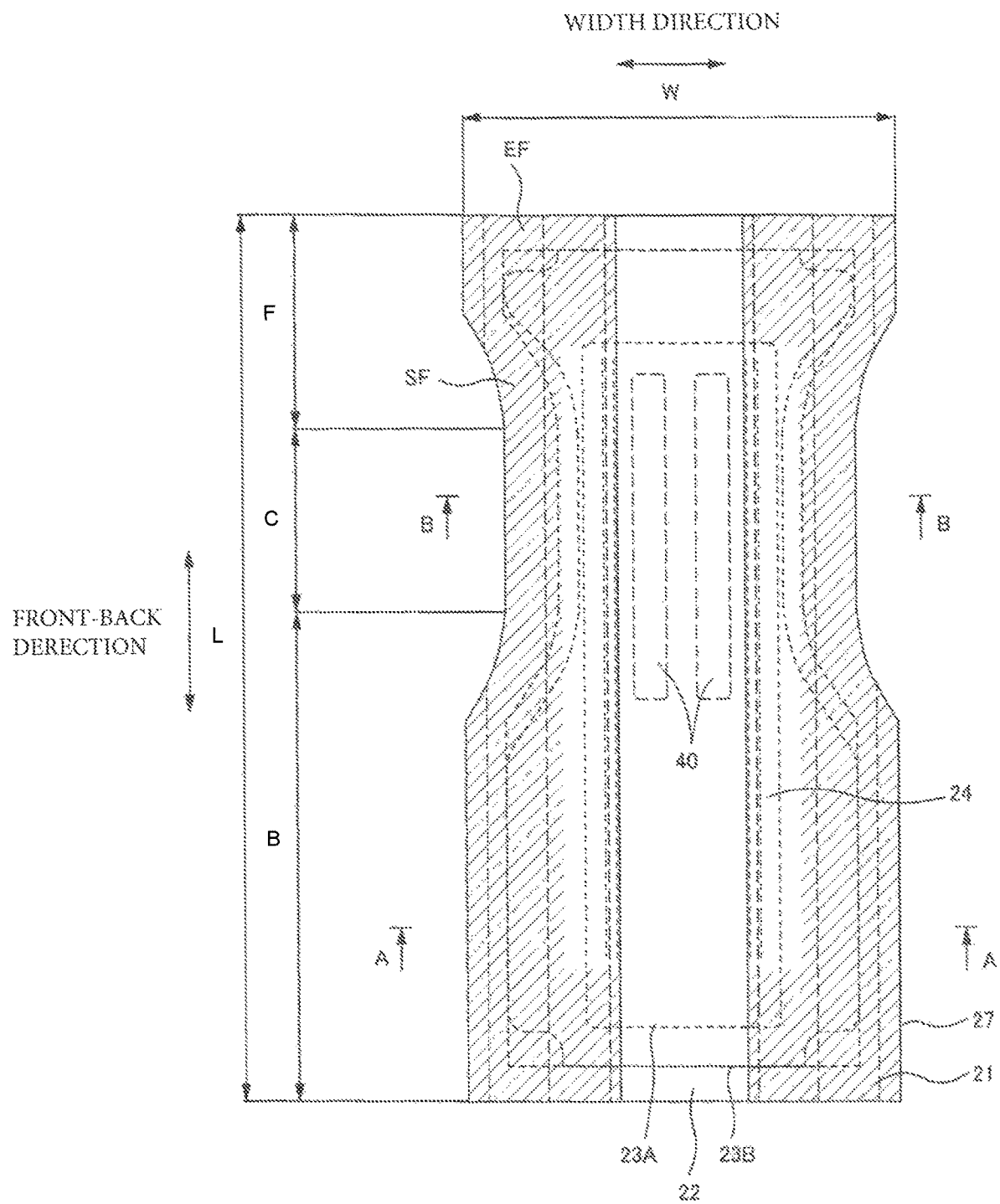
FIG. 1 is a plan view illustrating an inner surface of a pad in a spread state.
Figure 2:
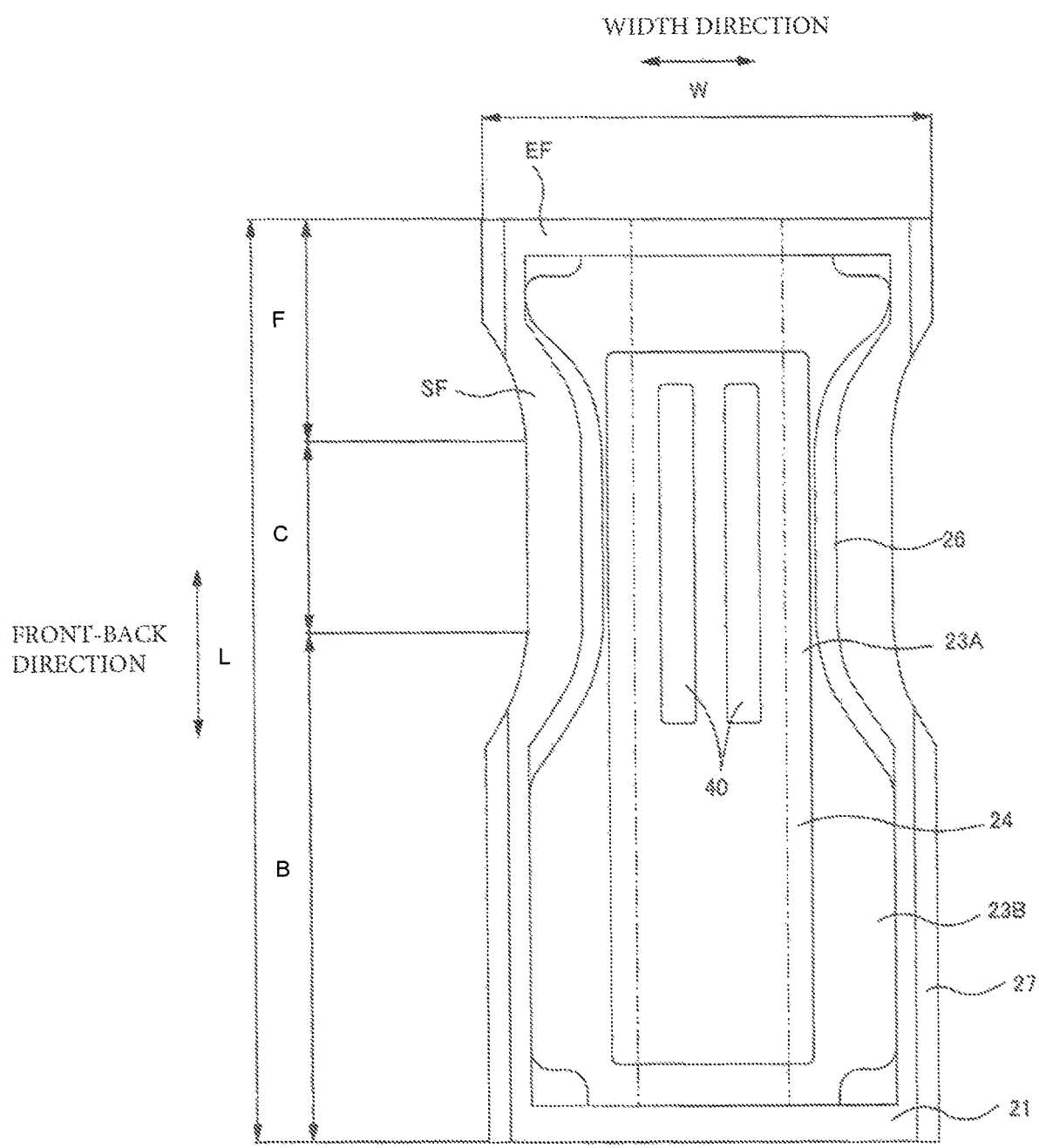
FIG. 2 is a plan view illustrating only essential portions.
Figure 3:
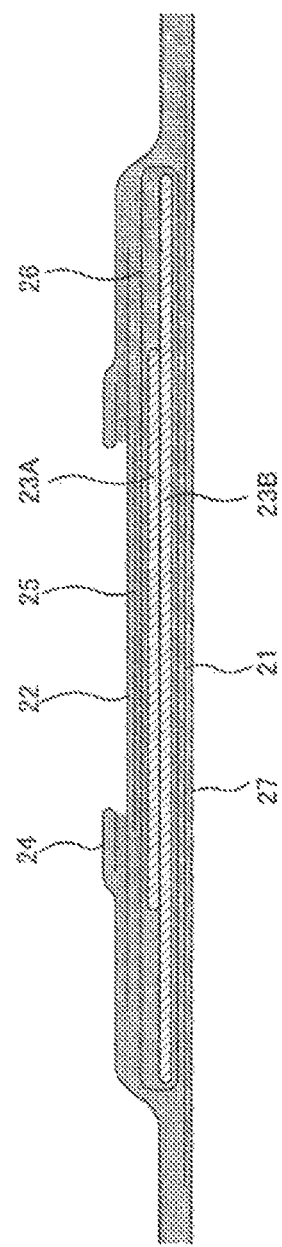
FIG. 3 is a cross-sectional view taken along line A-A of FIG. 1.

As illustrated in FIGS. 1 to 4, the pad of the first embodiment includes a crotch portion C, a front body F extending to the front side of the crotch portion C, and a back body B extending to the back side of the crotch portion C. For example, the size of each part can be appropriately determined. For example, it is possible to form the length L of the pad in the front-back direction to be 350 to 700 mm, the width W in the width direction to be 130 to 400 mm, the length in the front-back direction of the front body F to be 50 to 350 mm, the length of the crotch C in the front-back direction to be 10 to 150 mm, the length of the back body B in the front-back direction to be 50 to 350 mm, and the minimum width of the crotch portion C to be 200 to 260 cm.

The pad includes a liquid-impervious back-face sheet 21, a liquid-pervious front-face sheet 22, an absorber 23 disposed between the back-face sheet 21 and the front-face sheet 22, and the three-dimensional gathers 24 formed on both the side portions of the front-face sheet 22 in the width direction.

On the outer side of the absorber 23, the back-face sheet 21 is provided so as to slightly protrude from the outer peripheral edge of the absorber 23. As the back-face sheet 21, in addition to a polyethylene film or the like, a sheet having moisture permeability without impairing water interception can be used from the viewpoint of prevention of stuffiness. A microporous sheet can be used for this waterproof/moisture pervious sheet, and the microporous sheet is obtained by melt kneading an olefinic resin such as polyethylene resin and polypropylene resin, and inorganic filler, forming a sheet with the kneaded materials, and then uniaxially or biaxially stretching the sheet.

An outer sheet 27 made of a nonwoven fabric is provided on the outer side of the back-face sheet 21 so as to protrude slightly from the outer peripheral edge of the back-face sheet 21. As the outer sheet 27, various types of nonwoven fabrics can be used. As the material fibers constituting the nonwoven fabric, not only synthetic fibers of olefin type such as polyethylene or polypropylene, polyester type, amide type and the like, regenerated fiber such as rayon and cupra, natural fiber such as cotton can be used.

On the inside of the absorber 23, the front-face sheet 22 is provided. In the first embodiment, the width in the width direction of the front-face sheet 22 is narrower than the width in the width direction of the absorber 23, but the width in the width direction of the front-face sheet 22 can be formed wider than the width in the width direction of the absorber 23. As the front-face sheet 22, a porous or nonporous nonwoven fabric, a porous plastic sheet or the like is used. As the material fibers constituting the nonwoven fabric, not only synthetic fibers of olefin type such as polyethylene or polypropylene, polyester type, amide type and the like, regenerated fiber such as rayon and cupra, natural fiber such as cotton can be used.

Between the front-face sheet 22 and the absorber 23, an intermediate sheet 25 is provided. As the intermediate sheet 25, a material having low water retentivity and high liquid permeability, such as various nonwoven fabrics, mesh films, or the like, can be used.

The three-dimensional gathers 24 are provided on both side portions in the width direction of the front-face sheet 22. Each of the three-dimensional gathers 24 is formed of a fixed portion fixed to a side portion in the width direction of the outer sheet 27 and a main unit section extending from the fixed portion to the side portion of the inner surface of the front-face sheet 22 beyond the side portion in the width direction of the absorber 23 and the like. In addition, the front and back end portions of the main unit section in the front-back direction are fixed to the front-face sheet 22, and the central portion in the front-back direction of the main unit section is not fixed to the front-face sheet 22 but rises inward. In FIG. 1, the fixed portions of the three-dimensional gathers 24 are indicated by oblique lines.

Figure 4:
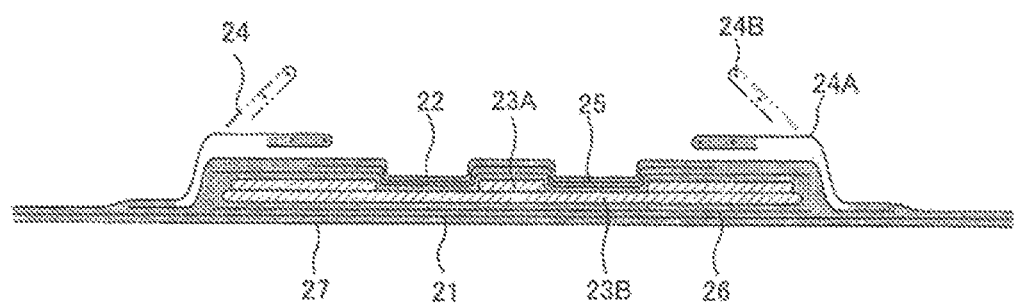
FIG. 4 is a cross-sectional view taken along line B-B of FIG. 1.

The three-dimensional gather 24 is formed of a double gather sheet 24A and an elongated elastic member 24B extending in the front-back direction. As the material of the gather sheet 24A, a plastic sheet or a meltblown nonwoven fabric can be used, but a water repellent treatment can be used for the nonwoven fabric with silicone or the like from the viewpoint of texture to the skin. In addition, as the elastic member 24B, the materials which are usually used, such as styrene rubber, olefin rubber, urethane rubber, ester rubber, polyurethane, polyethylene, polystyrene, styrene butadiene, silicone, polyester, and the like which are formed in a thread-like shape, a stripe-like shape, a band-like shape, and the like can be used. As illustrated in FIG. 4, the elastic member 24B makes the three-dimensional gather 24 rise inward by its stretching force.

At the front and back end portions in the front-back direction of the pad, the front-face sheet 22 and the outer sheet 27 are fixed to form end flap portions EF, and at both side end portions in the width direction of the pad, the gather sheets 24A and the outer sheet 27 are fixed to form side flap portions SF. Note that the absorber 23 does not extend in the end flap portions EF and the side flap portions SF.

The absorber 23 is formed of an inner absorber 23A positioned on the inner side of a wearer's body surface side and an outer absorber 23B positioned on the outer side. In addition, the inner absorber 23A and the outer absorber 23B are accumulated bodies of pulp fibers, assemblies of filaments such as cellulose acetate, or nonwoven fabrics, and as necessary, super absorbent polymer particles in the form of particulates, etc. can be mixed and fixed. In addition, it is preferable that the inner absorber 23A and the outer absorber 23B are wrapped with a wrapping sheet 26 such as crepe paper or the like in order to prevent super absorbent polymer particles from falling off or the like.

The outer absorber 23B is formed by a front side portion 30 positioned at the front body F of the pad, a narrowing portion 31 positioned at the crotch portion C of the pad, and a back side portion 32 positioned at the back body B of the pad. The narrowing portion 31 is formed by notching, in substantially trapezoidal shape, both side portions in the width direction positioned in the front side portion 30 and the back side portion 32 of the outer absorber 23B.

The minimum width of the narrowing portion 31 is formed to be 50 to 65% of the width W1 of the front side portion 30 and the back side portion 32. Further, when the front end of the outer absorber 23B is 0%, and the rear end of the outer absorber 23B is 100%, the front end of the narrowing portion 31 is disposed at 10 to 25%, the back end of the narrowing portion 31 is disposed at 40 to 65%, and a portion having the minimum width of the narrowing portion 31 is disposed at 25 to 30%.

The inner absorber 23A is formed in a substantially rectangular shape extending in the front-back direction at a predetermined interval in the width direction. The length in the front-back direction of the inner absorber 23A is formed to be 60 to 90% of the length L1 in the front-back direction of the outer absorber 23B, and the width in the width direction of the inner absorber 23A is formed to be 60% to 90% of the width W1 of in the width direction of the outer absorber 23B. In addition, in the inner absorber 23A, at a part facing the narrowing portion 31 of the outer absorber 23B, a pair of substantially rectangular slits 40 having a long side in the front-back direction and a predetermined length in the width direction is provided with a predetermined interval in the width direction.

Figure 5:
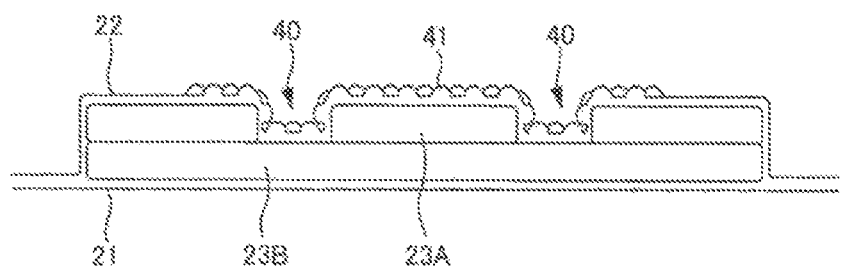
FIG. 5 is a cross-sectional view of convex portions of a front-face sheet.

As illustrated in FIG. 5, from the front-face sheet 22, in a part thereof facing the slits 40 of the inner absorber 23A, a large number of convex portions 41 protruding inward are formed in a staggered pattern with predetermined intervals in the front-back direction and width direction.

Figure 6:
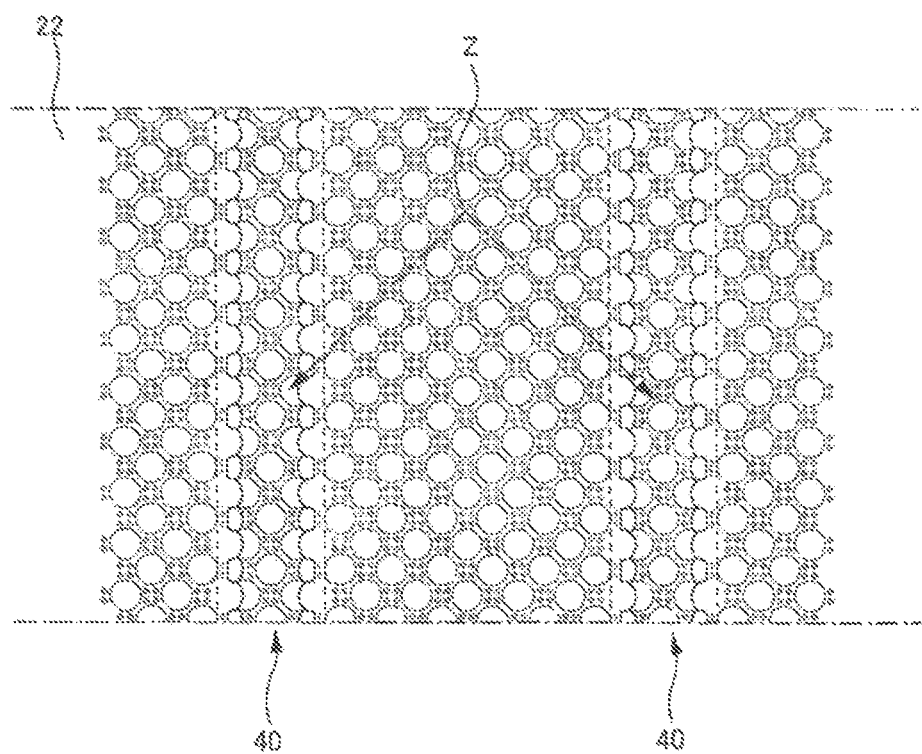
FIG. 6 is a plan view of the convex portions of the front-face sheet.

Accordingly, as illustrated in FIG. 6, urine excreted at an excreted position of urine Z on the front-face sheet 21 flows in oblique directions between the convex portions 41 protruding on the front-face sheet 21 and the adjacent convex portions 41, rather than flowing in the front-back direction or the width direction, a large amount of urine urinated at the excreted position of urine Z flows into the slits 40 formed at both sides of the excreted position of urine Z. Therefore, while suppressing the decrease in the absorbable amount, the crotch portion C has excellent fitting and also excellent anti-returning property.

The convex portion 41 can be formed by extruding the front-face sheet 22 from the outside to the inside by embossing. Further, the shape of the convex portion 41 can be formed in a circular shape, an elliptical shape, or a polygonal shape.

Next, a folding method of the pad for preventing the convex portion 41 projecting on the front-face sheet 22 from being crushed will be described. In the following description, a folding method of the outer absorber 23B in which the three-dimensional gathers 24, the front-face sheet 22, the inner absorber 23A, the back-face sheet 21, and the like of the pad are removed will be described for easy understanding.

Figure 7:
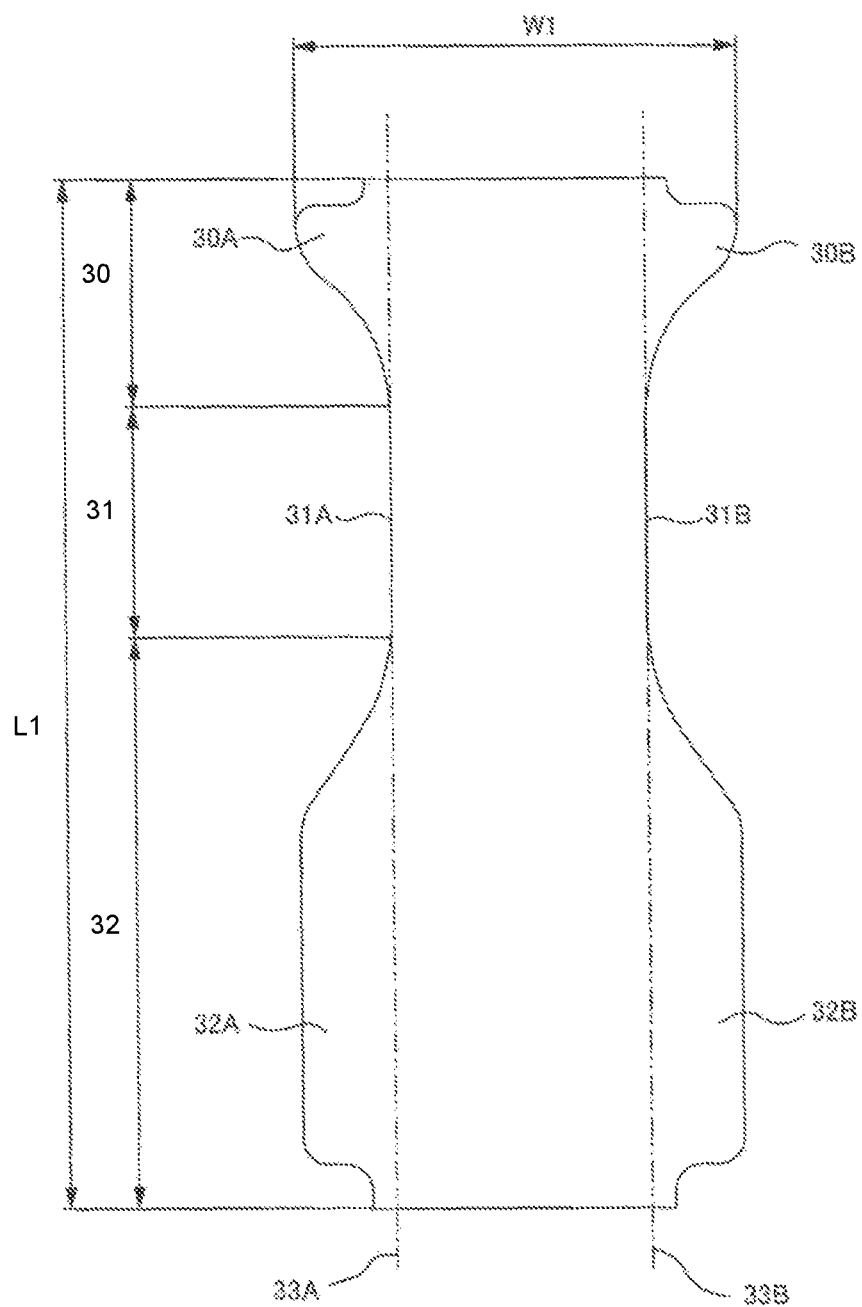
FIG. 7 is a plan view of an outer absorber in a spread state.
Figure 8:
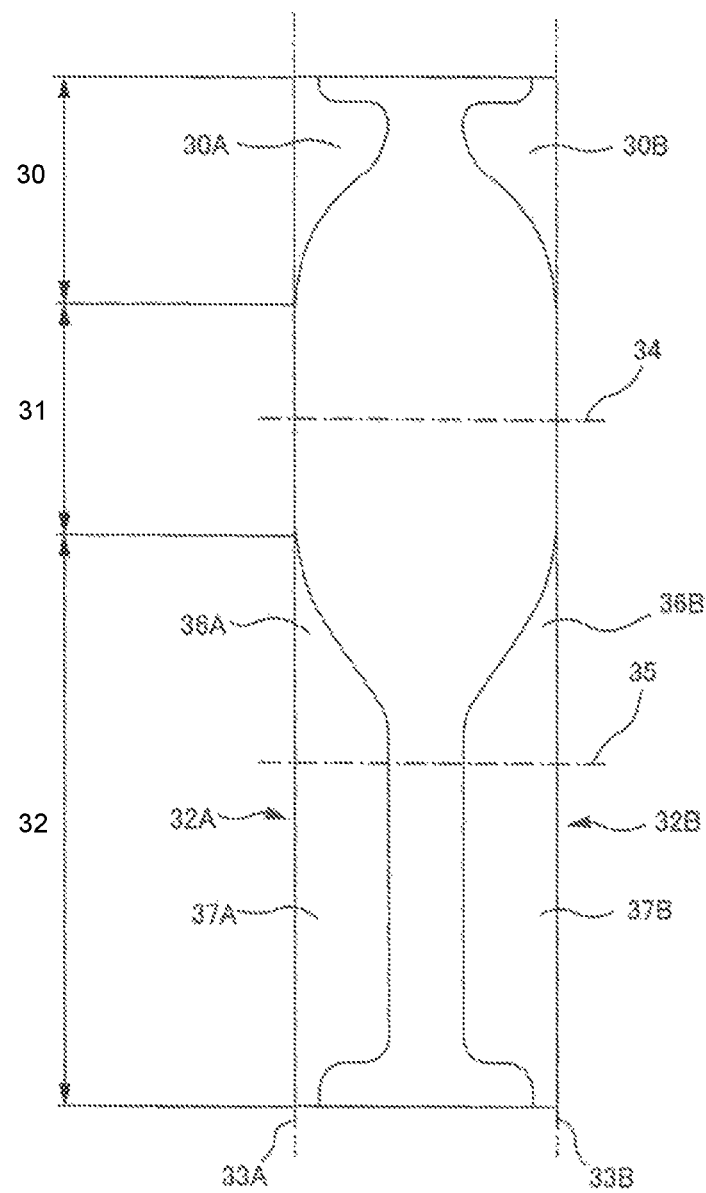
FIG. 8 is a plan view in which both side portions of the outer absorber are folded inward.

As illustrated in FIGS. 7 and 8, a left front side portion 30A of the front side portion 30 and a left back side portion 32A of the back side portion 32, which are positioned on the left side with respect to a first left side folding line 33A, are folded inward with the first left side folding line 33A, which is extending in an imaginary front-back direction as the center for the folding and which is positioned on a left side narrowing edge 31A that forms the left end portion having the minimum width in the narrowing portion 31 of the outer absorber 23B. Similarly, a right front side portion 30B of the front side portion 30 and a right back side portion 32B of the back side portion 32, which are positioned on the right side with respect to a first right side folding line 33B, are folded inward with the first right side folding line 33B, which is extending in an imaginary front-back direction as the center for the folding and which is positioned on a right side narrowing edge 31B that forms the right end portion having the minimum width in the narrowing portion 31 of the outer absorber 23B. The first left side folding line 33A and the first right side folding line 33B are collectively referred to as a first folding line 33. In addition, the first left side folding line 33A is set at a position deviated from the left side narrowing edge 31A of the narrowing portion 31 to the left side narrowing edge 31A in the width direction of the left front side portion 30A, and the first right side folding line 33B is set at a position deviated from the right side narrowing edge 31B of the narrowing portion 31 to the right side narrowing edge 31B in the width direction of the right front side portion 30B.

Figure 9:
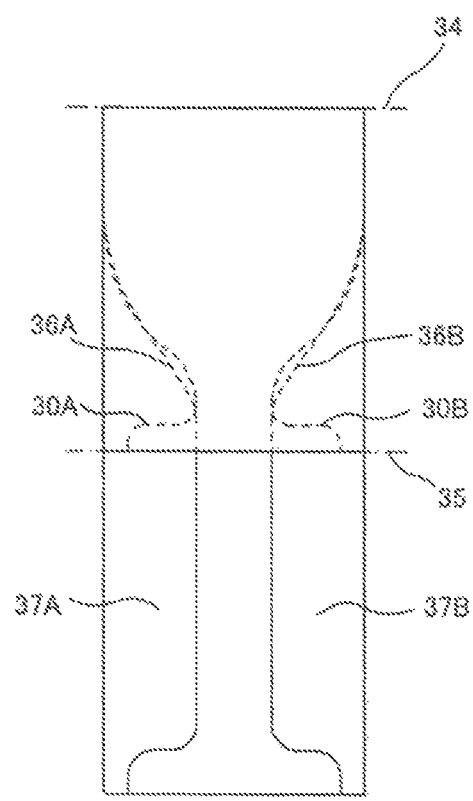
FIG. 9 is a plan view in which the front side portion of the outer absorber is folded inward.

Next, as illustrated in FIGS. 8 and 9, the front side portion 30, in a state where the left front side portion 30A and the right front side portion 30B are folded, is folded inward with the second folding line 34 which is positioned on the front side of the second and third folding lines 34 and 35 extending in the width direction that approximately trisect the outer absorber 23B in the front-back direction.

Figure 11:
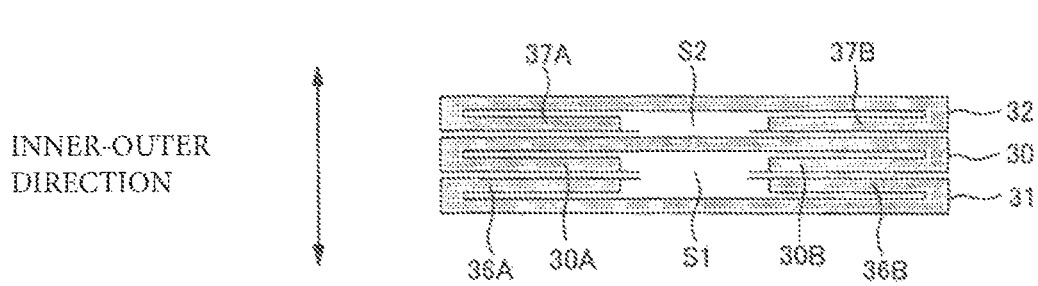
FIG. 11 is a cross-sectional view taken along line A-A of FIG. 10.
Figure 12:
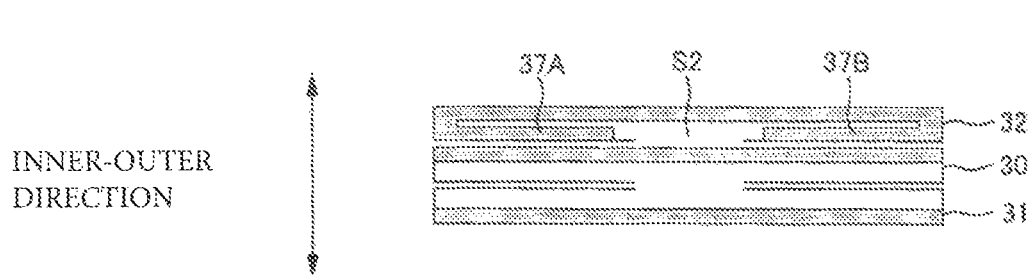
FIG. 12 is a cross-sectional view taken along line B-B of FIG. 10.
Figure 13:
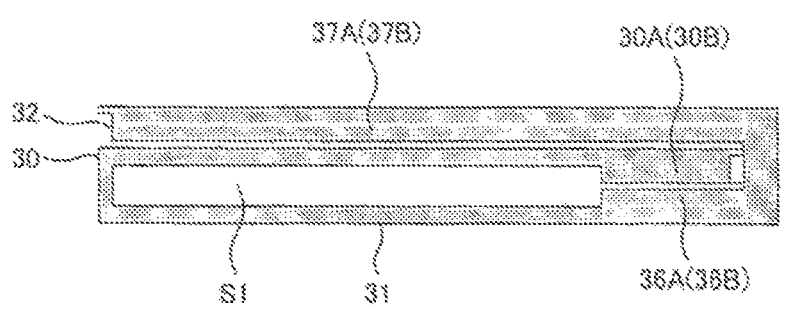
FIG. 13 is a cross-sectional view taken along line C-C of FIG. 10.

As a result, an outer surface of the left front side portion 30A overlaps on an outer surface of the first left back side portion 36A extending to the front side with respect to the third folding line 35 in the left back side portion 32A, and an outer surface of the right front side portion 30B overlaps on an outer surface of the first right back side portion 36B extending on the front side with respect to the third folding line 35 in the right back side portion 32B. As illustrated in FIGS. 11 and 12, a large space S1 is formed between an inner surface of the narrowing portion 31 at the central portion in the width direction and an inner surface of the front side portion 30. Accordingly, the protruding convex portions 41 of the front-face sheet 22 positioned at the central portion in the width direction of the front side portion 30 are not pressed by the inner face of the narrowing portion 31, and the protruding convex portions 41 of the front-face sheet 22 positioned at the central portion in the width direction of the front-face sheet 22 are not pressed by the inner face of the front side portion 30, so that the shapes of the convex portions 41 can be maintained. Further, as illustrated in FIG. 13, since the space S1 is formed in a site deviated to the front side of the narrowing portion 31, and the convex portions 41 in the vicinity of the excreted position of urine Z can be maintained, it is possible to suppress the decrease in the absorbable amount so as to maintain a pad in which the crotch portion C has excellent fitting and excellent anti-returning property.

Figure 10:
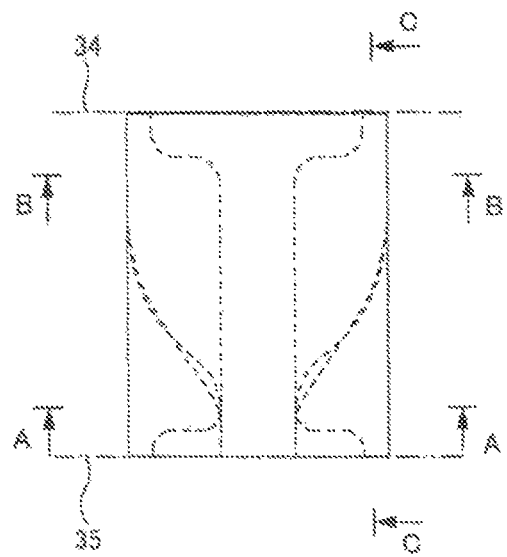
FIG. 10 is a plan view in which the back side portion of the outer absorber are folded inward.

Next, as illustrated in FIGS. 9 and 10, the back side portion 32, in a state where the left back side portion 32A and the right back side portion 32B are folded with the third folding line 35 as the center for the folding, is folded inward.

As a result, an outer surface of the second left back side portion 37A extending to the back side with respect to the third folding line 35 in the left back side portion 32A overlaps on an outer surface of the front side portion 30, and an outer surface of the second right back side portion 37B extending on the back side with respect to the third folding line 35 in the right back side portion 32B overlaps on an outer surface of the front side portion 30. As illustrated in FIGS. 11 and 12, a space S2 is formed between an outer surface of the narrowing portion 31 at the central portion in the width direction and an inner surface of the back side portion 32. Therefore, the protruding convex portions 41 of the front-face sheet 22 positioned at the central portion in the width direction of the back side portion 32 suppress pressing by an outer surface of the narrowing portion 31, and the shapes of the convex portions 41 can be maintained. Note that the height in an inner-outer direction of the space S2 is substantially half of the height in the inner-outer direction of the space S1, and the level of maintaining the shapes of the convex portions 41 is low.

In the first embodiment, after the left back side portion 32A and the right back side portion 32B are folded inward with the third folding line as the center for the folding, the left front side portion 30A and the right front side portion 30B can be folded inward with the second folding line as the center for the folding.

Figure 14:
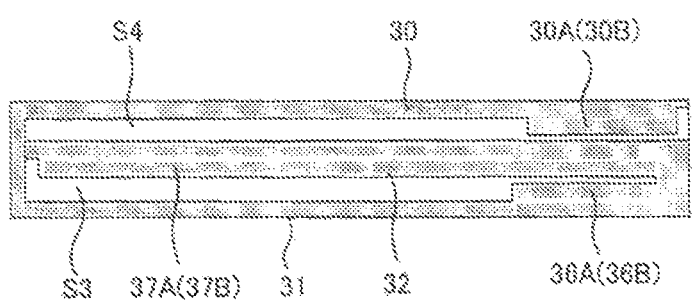
FIG. 14 is a cross-sectional view corresponding to a cross-sectional view taken along line C-C of FIG. 10 in a state where the front side portion of the outer absorber is folded inward after the back side portion of the outer absorber is folded inward.

As a result, as illustrated in FIG. 14, the space S3 is formed on an inner surface of the narrowing portion 31 and an inner surface of the outer portion 32, and the space S4 is formed between an outer surface of the outer portion 32 and an inner surface of the front side portion 30. Therefore, the shapes of the convex portions 41 on the inner surfaces of the narrowing portion 31 and the outer portion 32, and the convex portions 41 on the inner surface of the front side portion 30 can be maintained. Note that the heights in the inner-outer direction of the spaces S3 and S4 are substantially half of the height of the space S1 in the inner-outer direction, and the level of maintaining the shapes of the convex portions 41 is low.

Second Embodiment

Figure 15:
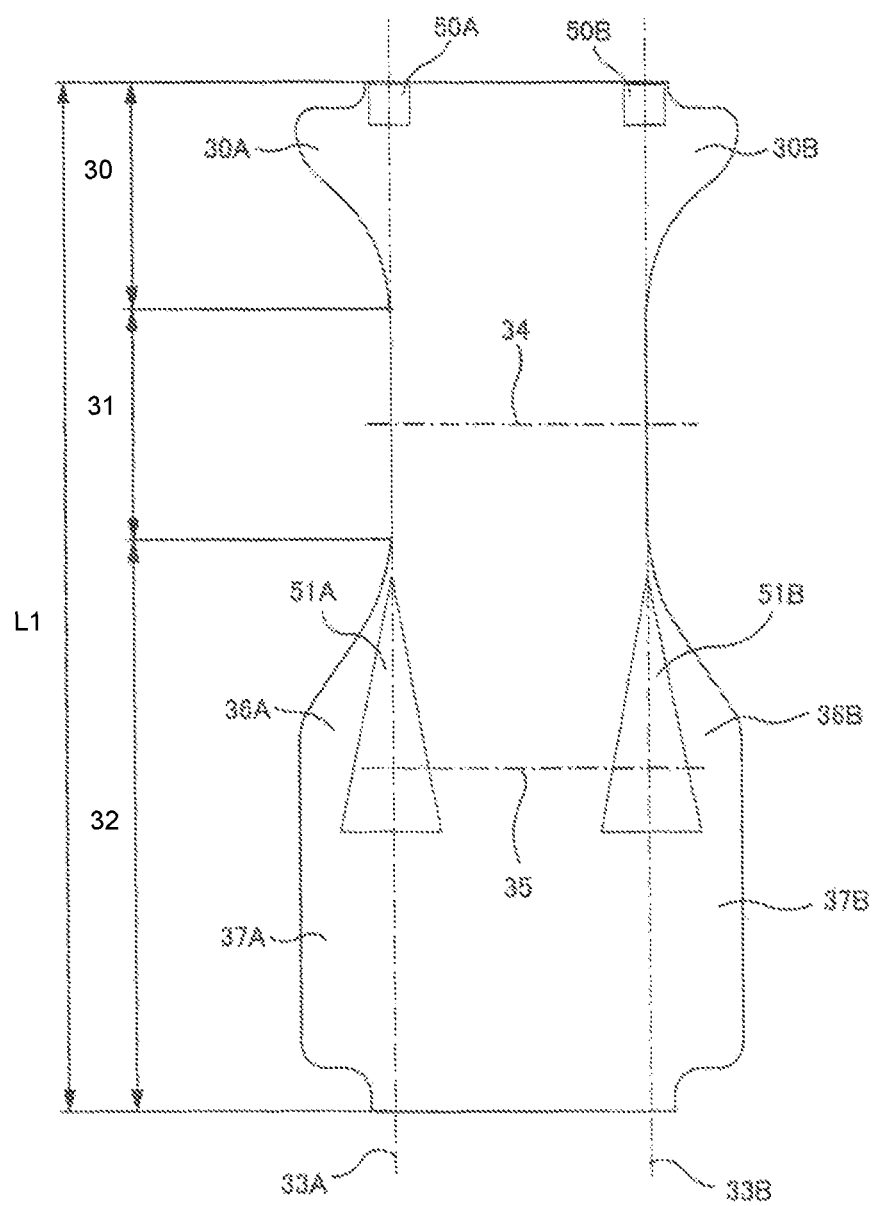
FIG. 15 is a plan view of an outer absorber according to a second embodiment.

Next, a pad according to a second embodiment will be described. The same parts as those of the pad according to the first embodiment are denoted by the same reference signs, and description thereof will be omitted. As illustrated in FIG. 15, at sites facing the first left side folding line 33A and the second right side folding line 33B at an end portion in the front-back direction of the outer absorber 23B, a first left front side overlapping portion 50A and a first right front side overlapping portion 50B each having a rectangular shape and extending in the front-back direction with a predetermined length in the width direction are provided. The first left front side overlapping portion 50A and the first right front side overlapping portion 50B can be formed by increasing the weight per unit area of each accumulated body of pulp fibers or the like forming the outer absorber 23B.

A second left back side overlapping portion 51A and a second right back side overlapping portion 51B which are substantially triangular in shape are provided at sites facing the third folding line 35 in both side portions in the width direction of the outer absorber 23B. In addition, the front side portion of the second left back side overlapping portion 51A extends to the front side with respect to the third folding line 35, and the back side portion of the second left back side overlapping portion 51A extends to the back side with respect to the third folding line 35. Similarly, the front side portion of the second right back side overlapping portion 51B extends to the front side with respect to the third folding line 35, and the back side portion of the second right back side overlapping portion 51B extends to the back side with respect to the third folding line 35. In addition, the second left back side overlapping portion 51A and the second right back side overlapping portion 51A can be formed by increasing the weight per unit area of each accumulated body of pulp fibers or the like forming the outer absorber 23B.

Consequently, by increasing the height in the inner-outer direction of the space S1 formed when the outer absorber 23B is folded inward with the first folding line 33 as the center for the folding, the front side portion 30 of the outer absorber 23B is folded inward with the second folding line 34 as the center for the folding, and the back side portion 32 of the outer absorber 23B is folded inward with the third folding line 35 as the center for the folding, it is possible to further maintain the shapes of the convex portions 41 of the front-face sheet 22 positioned at the central portion of the front side portion 30 and the convex portions 41 of the front-face sheet 22 positioned at the central portion of the narrowing portion 31.

Third Embodiment

Figure 16:
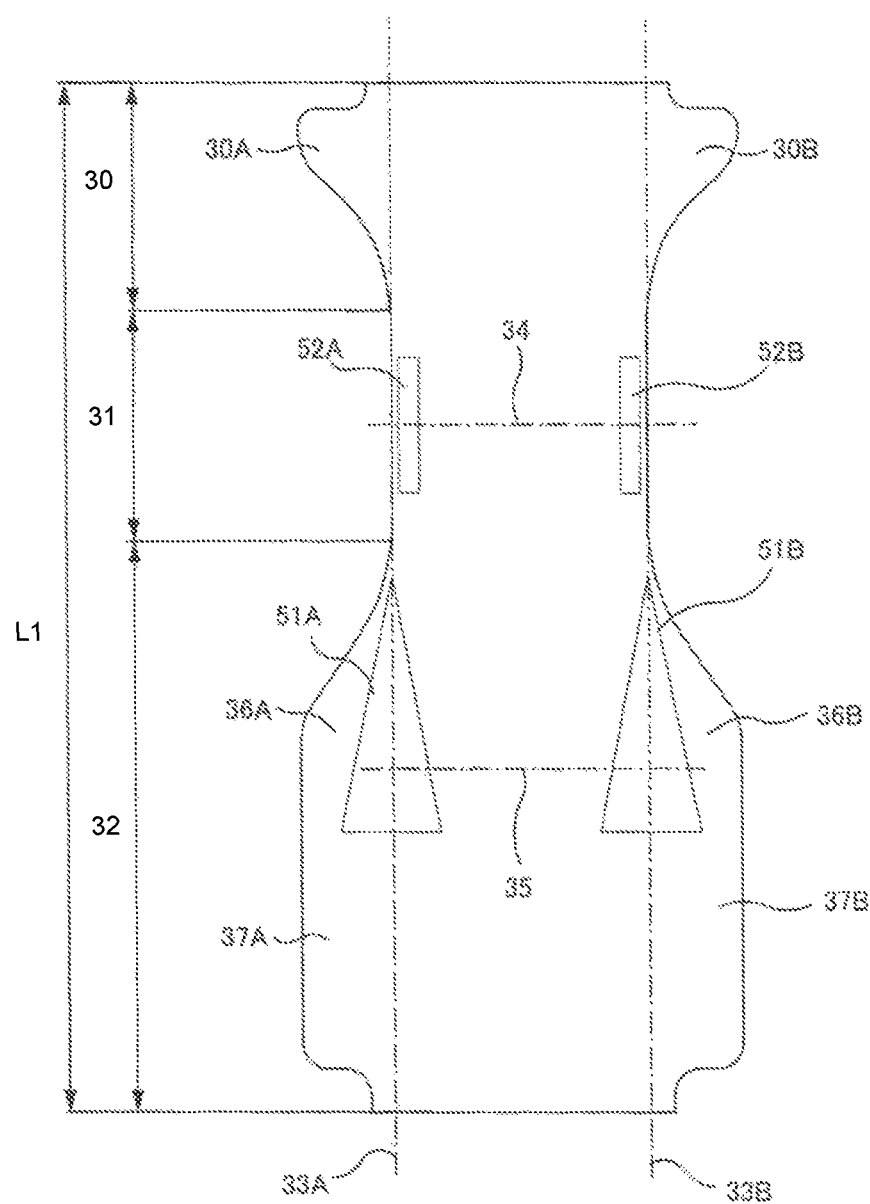
FIG. 16 is a plan view of an outer absorber according to a third embodiment.

Next, a pad according to a third embodiment will be described. The same members as those of the pad according to the first embodiment are denoted by the same reference signs, and description thereof will be omitted. As illustrated in FIG. 16, the third left middle side overlapping portion 52A and the third right middle side overlapping portion 52B each having a rectangular shape and extending in the front-back direction with a predetermined length in the width direction are provided at sites facing the second folding line 34 in both the side portions in the width direction of the outer absorber 23B. Further, the front side portion of the third left middle side overlapping portion 52A extends to the front side with respect to the second folding line 34, and the back side portion of the third left middle side overlapping portion 52A extends to the back side with respect to the second folding line 34. Similarly, the front side portion of the third right middle side overlapping portion 52B extends to the front side with respect to the second folding line 34, and the back side portion of the third right middle side overlapping portion 52B extends to the back side with respect to the second folding line 34. In addition, the third left middle side overlapping portion 52A and the third right middle side overlapping portion 52B can be formed by increasing the weight per unit area of each accumulated body of pulp fibers or the like forming the outer absorber 23B.

A second left back side overlapping portion 51A and a second right back side overlapping portion 51B which are substantially triangular in shape are provided at sites facing the third folding line 35 in both side portions in the width direction of the outer absorber 23B. In addition, the front side portion of the second left back side overlapping portion 51A extends to the front side with respect to the third folding line 35, and the back side portion of the second left back side overlapping portion 51A extends to the back side with respect to the third folding line 35. Similarly, the front side portion of the second right back side overlapping portion 51B extends to the front side with respect to the third folding line 35, and the back side portion of the second right back side overlapping portion 51B extends to the back side with respect to the third folding line 35. In addition, the second left back side overlapping portion 51A and the second right back side overlapping portion 51A can be formed by increasing the weight per unit area of each accumulated body of pulp fibers or the like forming the outer absorber 23B.

Consequently, by increasing the height in the inner-outer direction of the space S1 formed when the outer absorber 23B is folded inward with the first folding line 33 as the center for the folding, the front side portion 30 of the outer absorber 23B is folded inward with the second folding line 34 as the center for the folding, and the back side portion 32 of the outer absorber 23B is folded inward with the third folding line 35 as the center for the folding, it is possible to further maintain the shapes of the convex portions 41 of the front-face sheet 22 positioned at the central portion of the front side portion 30 and the convex portions 41 of the front-face sheet 22 positioned at the central portion of the narrowing portion 31.

INDUSTRIAL APPLICABILITY

The present invention is applicable to an absorbent article.

REFERENCE SIGNS LIST 21 back-face sheet
22 front-face sheet
23 absorber
30 front side portion
30A left front side portion
30B right front side portion
31 narrowing portion
31A left side narrowing edge
31B right side narrowing edge
32 back side portion
32A left back side portion
32B right back side portion
33A first left side folding line
33B first right side folding line
34 second folding line
35 third folding line
36A first left back side portion
36B first right back side portion
41 convex
50A first left front side overlapping portion
50B first right front side overlapping portion
51A second left back side overlapping portion
51B second right back side overlapping part
52A third right middle side overlapping portion
52B third right middle side overlapping portion

The invention claimed is:

1. A pad comprising a liquid-pervious front-face sheet, a liquid-impervious back-face sheet, and an absorber disposed between the front-face sheet and the back-face sheet, wherein
convex portions are formed to protrude on the front-face sheet,
the absorber is formed with a front side portion positioned on a front side in a front-back direction, a narrowing portion positioned in a central portion in the front-back direction, and a back side portion positioned on a back side in the front-back direction,
in a planar view, a left front side portion of the front side portion is extended to a left side with respect to a left side narrowing edge of a narrowest portion of the narrowing portion, and a right front side portion of the front side portion is extended to a right side with respect to a right side narrowing edge of the narrowest portion of the narrowing portion,
in the planar view, a left back side portion of the back side portion is extended to the left side with respect to the left side narrowing edge of the narrowest portion of the narrowing portion, and a right back side portion of the back side portion is extended to the right side with respect to the right side narrowing edge of the narrowest portion of the narrowing portion,
the left front side portion and the left back side portion are folded inward with a first left side folding line, which is extending in the front-back direction as a center for folding and which is provided close to the left side with respect to the left side narrowing edge,
the right front side portion and the right back side portion are folded inward with a first right side folding line which is extending in the front-back direction as a center for folding and which is provided close to the right side with respect to the right side narrowing edge,
in the planar view, a second folding line extending in a width direction is provided on the front side of two positions at which the absorber is divided into three in the front-back direction, and a third folding line extending in the width direction is provided on the back side of the two positions,
the front side portion, in a state where the left front side portion and the right front side portion are folded, is folded inward with the second folding line as a center for folding, or the back side portion, in a state where the left back side portion and the right back side portion are folded, is folded inward with the third folding line as a center for folding,
after that, the back side portion, in a state where the left back side portion and the right back side portion are folded, is folded inward with the folding line as a center for folding or the front side portion, in a state where the left front side portion and the right front side portion are folded, is folded inward with the third folding line as a center for folding, and
the first left side folding line is positioned on the left side narrowing edge, and the first right side folding line is positioned on the right side narrowing edge.

2. The pad according to claim 1, wherein a first left front side overlapping portion and a first right front side overlapping portion each having a rectangular shape are provided at sites overwrapping with the first left side folding line and the first right side folding line, respectively in a front portion of the front side portion,
a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

3. The pad according to claim 1, wherein a third left middle side overlapping portion and a third right middle side overlapping portion each having a rectangular shape are provided at sites overlapping with the second folding line on both sides of the narrowing portion, a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

4. A pad comprising a liquid-pervious front-face sheet, a liquid-impervious back-face sheet, and an absorber disposed between the front-face sheet and the back-face sheet, wherein convex portions are formed to protrude on the front-face sheet, the absorber is formed with a front side portion positioned on a front side in a front-back direction, a narrowing portion positioned in a central portion in the front-back direction, and a back side portion positioned on a back side in the front-back direction, in a planar view, a left front side portion of the front side portion is extended to a left side with respect to a left side narrowing edge of a narrowest portion of the narrowing portion, and a right front side portion of the front side portion is extended to a right side with respect to a right side narrowing edge of the narrowest portion of the narrowing portion, in the planar view, a left back side portion of the back side portion is extended to the left side with respect to the left side narrowing edge of the narrowest portion of the narrowing portion, and a right back side portion of the back side portion is extended to the right side with respect to the right side narrowing edge of the narrowest portion of the narrowing portion, the left front side portion and the left back side portion are folded inward with a first left side folding line, which is extending in the front-back direction as a center for folding and which is provided close to the left side with respect to the left side narrowing edge, the right front side portion and the right back side portion are folded inward with a first right side folding line which is extending in the front-back direction as a center for folding and which is provided close to the right side with respect to the right side narrowing edge, in the planar view, a second folding line extending in a width direction is provided on the front side of two positions at which the absorber is divided into three in the front-back direction, and a third folding line extending in the width direction is provided on the back side of the two positions, the front side portion, in a state where the left front side portion and the right front side portion are folded, is folded inward with the second folding line as a center for folding, the left front side portion is disposed on an inner side of the first left back side portion extending on the front side with respect to the third folding line in the left back side portion, the right front side portion is disposed on an inner side of the first right back side portion extending on the front side with respect to the third folding line in the right back side portion, after that, the back side portion, in a state where the left back side portion and the right back side portion are folded, is folded inward with the third folding line as a center for folding, and the first left side folding line is positioned on the left side narrowing edge, and the first right side folding line is positioned on the right side narrowing edge.

5. The pad according to claim 4, wherein a first left front side overlapping portion and a first right front side overlapping portion each having a rectangular shape are provided at sites overwrapping with the first left side folding line and the first right side folding line, respectively in a front portion of the front side portion, a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

6. The pad according to claim 4, wherein a third left middle side overlapping portion and a third right middle side overlapping portion each having a rectangular shape are provided at sites overlapping with the second folding line on both sides of the narrowing portion, a second left back side overlapping portion and a second right back side overlapping portion each having a triangular shape and having a top portion on the front side are provided at sites overlapping with the first left side folding line and the first right side folding line, respectively in a front portion of the back side portion, and the second left back side overlapping portion and the second right back side overlapping portion are each extended to the front side with respect to the third folding line.

\* \* \* \* \*